United States Patent
Rigoletto, Jr. et al.

(10) Patent No.: US 7,837,983 B2
(45) Date of Patent: Nov. 23, 2010

(54) MENDING HAIR DAMAGE WITH POLYELECTROLYTE COMPLEXES

(75) Inventors: Raymond Rigoletto, Jr., Denville, NJ (US); Yan Zhou, Montville, NJ (US)

(73) Assignee: ISP Investments Inc., Wilmington, DE (US)

( * ) Notice: Subject to any disclaimer, the term of this patent is extended or adjusted under 35 U.S.C. 154(b) by 681 days.

(21) Appl. No.: 11/484,251

(22) Filed: Jul. 11, 2006

(65) Prior Publication Data

US 2006/0251603 A1 Nov. 9, 2006

Related U.S. Application Data

(63) Continuation-in-part of application No. 10/890,651, filed on Jul. 14, 2004, now abandoned.

(51) Int. Cl.
*A61K 8/72* (2006.01)
(52) U.S. Cl. .................................................. 424/70.11
(58) Field of Classification Search ........................ None
See application file for complete search history.

(56) References Cited

U.S. PATENT DOCUMENTS

| | | | |
|---|---|---|---|
| 4,299,817 A | 11/1981 | Hannan et al. | |
| 4,900,545 A | 2/1990 | Wisotzki et al. | |
| 5,843,193 A * | 12/1998 | Hawkins et al. | ................. 8/408 |
| 6,071,505 A | 6/2000 | Manuszak-Guerrini et al. | |
| 6,106,815 A * | 8/2000 | Kang et al. | ............... 424/70.12 |
| 6,110,451 A * | 8/2000 | Matz et al. | ............... 424/70.16 |
| 6,139,851 A | 10/2000 | Omura et al. | |
| 6,251,379 B1 | 6/2001 | Omura et al. | |
| 6,258,348 B1 | 7/2001 | Tsivkin | |
| 6,696,067 B2 * | 2/2004 | Brandt et al. | ................ 424/401 |

FOREIGN PATENT DOCUMENTS

| EP | 0566049 | 4/1993 |
|---|---|---|
| WO | 96/32920 | 10/1996 |

* cited by examiner

*Primary Examiner*—Robert A Wax
*Assistant Examiner*—Bethany Barham
(74) *Attorney, Agent, or Firm*—William J. Davis; Thompson Hine LLP

(57) ABSTRACT

Polyelectrolyte complexes between anionic and cationic polymers are used to mend damaged hair fibers, especially damage exhibited by split ends. An improved test method designed for the assessment of the degree of split end repair is described which consists of tagging hair fibers and observing the repair process by stereomicroscopy.

38 Claims, 7 Drawing Sheets

Particle Size Distributions of the
PEC Microgels of Invention

PEC Microgel Images of Example 1

1.8% active Conditioneze NT-20 and 0.20% Gantrez S-97

PEC Microgel Images of Example 7

0.51% Styleze 2000 and 1.49% active Conditioneze NT-20

PEC Microgel Images of Example 8

0.25% Polymethylvinyl ether/maleic acid (Gantrez S-97)
and 1.75% Polyquaternium 10 (Polyquta 400 KC)

PEC Microgel Images of Example 9a 0.25% Polymethylvinyl ether/maleic acid (Gantrez S-97)

and 1.75% active Polyquaternium-7 (Conditioneze-7)

Microscope Images of Comparative Example 9b 0.25% Polymethylvinyl ether/maleic acid (Gantrez S-97)

and 1.25% active Polyquaternium-7 (Conditioneze-7)

Precipitate PEC, non microgel structure

Mending Efficacy of PEC Compositions vs Charge ratios

MENDING HAIR DAMAGE WITH POLYELECTROLYTE COMPLEXES

CROSS REFERENCE TO RELATED U.S. PATENT APPLICATION

This application is a continuation-in-part of U.S. patent application Ser. No. 10/890,651, filed on Jul. 14, 2004 now abandoned, the complete disclosure of which is hereby incorporated by reference herein.

BACKGROUND OF THE INVENTION

1. Field of the Invention

This invention relates to hair care compositions, and, more particularly, to hair repair compositions for mending damaged fibers such as split ends of hair fibers.

2. Description of the Prior Art

The technical term for split ends is trichoptilosis. It is defined as a longitudinal splitting of the hair fiber which develops after the protective cuticle has been stripped away from the end of the hair fibers as a result of either physical or chemical traumatizing of the hair. Formation of split ends develops because of the fine structure of hair and the forces that are at work in its components.

There is a sequence of mechanical events that occur in the formation of split ends. During the combing process, fibers tend to snarl as the comb approaches the tip ends of the hair. It can be observed in these entanglements that the fibers are bent to various degrees. Since hair is elliptical and has a major and a minor axis, this bend occurs parallel to the major axis. The bending effect subjects the hair to longitudinal shear stresses parallel to the major elliptical axis. The magnitude of these shear forces are parabolically distributed across the minor axial diameter of the elliptical section. As hairs are being bent, these shear stresses will result in fracture and will propagate along the major elliptical axis resulting in a split end. The fibers bend as they pass through the prongs of a comb.

The disulfide bond in hair is another factor in split end formation. Protein molecules in the cortex of the hair fiber are crosslinked by covalent disulfide bonds, which provides strength and flexibility. During chemical processing, or through environmental damage, these bonds tend to break which makes the hair more susceptible to mechanical damage. The result is that damaged hair is more prone to splits and cracks during the combing and brushing process.

Split ends are more prone in hair that has been damaged by weathering, chemical treatments, or mechanical damage. Prevention of split ends generally involves adding lubricity to the hair with cationic surfactants so that there is less friction during combing resulting in less snarling. Also, adding plasticizing agents, which allows the hair to bend with more facility, will reduce split ends. Since water is a plasticizing agent, it is expected that fewer split ends will be produced at a high relative humidity, particularly, with the application of humectants that allows for moisturization.

Lubricating agents that can prevent or minimize formation of split ends include cationic surfactants commonly found in creme rinses, e.g. cetrimonium chloride, stearalkonium chloride, dicetyldimonium chloride, and behentrimonium methosulfate. Cationic polymers are more common lubricating agents found in shampoos. These polymers include polyquaternium compounds such as polyquaternium-6, -7, -10, -11, and -28. Guar hydroxypropyltrimonium chloride also is used as a lubricant. The mechanism by which such conditioner reduces damage during combing is based upon lubricity. The lubrication reduces the friction in the hair during combing and hence reduces the strength of the abrasive forces to which the hair is being subjected. This in turn reduces the number of entanglements during the combing process.

Plasticizing agents including humectants such as glycerin, propylene glycol, acetamide MEA, and sorbitol also are used for this purpose. An example of a substantive humectant containing a positive charge is Quaternium®-22 (Ceraphyl® 60). By treating the hair with conditioners that provide these properties it is possible to prevent the formation of split ends.

This invention, however, is concerned with split end repair and mending rather than prevention.

Prior Methods of Producing and Assessing Prevention of Split Ends

A mechanical device has been described in the literature to generate split ends. It consists of a motor driven rotary arm to which two combs are attached. A hair swatch is clamped into place so that the ends of the hairs are struck by the rotary arm. A linear relationship was established by Cooper between the time of exposure and the number of split ends generated. Hair treatment such as shampoos, conditioners and mousses reduced the number of split ends produced, however, studies are not conducted to affect their repair. Prevention was determined by comparing the percentage of hairs split in the hair swatches that were treated with different conditioning preparations. No explanation was provided, however, as to how this percentage is derived, or whether it is based on a sample of fibers from the tress or based on all the fibers in the tress.

Kon et al in J. Cosmet. Sci. 20, 361-380 (1998) also developed a method for artificially inducing damage to hair in order to serve as a model for studying the effect of ingredients on hair damage. Two models are described, one for scale lift and one for split hair, both having their own characteristic method. The split hair model consists of soaking the hair in a reducing solution that extracts a certain quantity of cortical protein from the hair fiber. After a detailed procedure of washing, de-lipidation, drying, reducing, washing, re-oxidizing, and lyophilizing (freeze-drying), the hairs are viewed for splits with an SEM. They postulated that the driving force for the split is osmotic shock. With this technique it was found that keratin peptides and cationic hydroxyethylcellulose have a preventative effect on split formation. These test solutions are added in between the reducing and oxidizing steps of the test method. Their explanation for adding these ingredients in the middle of the process is the fact that they prevent expansion of the split hairs during the lyophilization stage. They mention that peptides of low molecular weight can do this because they are more penetrative, and cationic derivatives because of their high affinity for the cortical proteins. Kon mentions that the method by Cooper has low reproducibility.

Split End Repair and Prevention Methodology

U.S. Pat. No. 6,071,505 described a water soluble quaternary ammonium cellulosic derivative of controlled charge density. It mentions many uses of these novel compounds applicable in both hair and skin care products. One such use is that it can mend split ends. However, no substantiation was given in the patent and there is no test method revealed as to how split end mending is achieved.

A brochure by Amerchol Corporation stated that all grades of UCARE® Polymer can mend split ends. The method described is as follows. " . . . individual strands of virgin brown hair were mounted on a plastic stand for each shampoo to be tested. Each hair was then shampooed by inserting the individual hair into an eyedropper containing the test formulation. The strand was then rinsed with distilled water from a squeeze bottle and the process was repeated to simulate normal shampoo procedure. The hairs were examined immediately by hand lens for mended splits, and again after drying one hour at 54° C. (129° F.). To simulate combing, each hair was "tickled" ten times with a spatula and the number of splits still mended was recorded. After one hour at room temperature, the hairs were again examined." Results indicate that at every stage of the experiment, UCARE® Polymer containing shampoos provide for 100% mending of split ends. The control shampoo containing just TEA Lauryl Sulfate and Cocamide DEA provided for 70% mending. With this method the combing simulation did not subject the hair to enough stress that actual combing provides. Also, the 70% mending rate for the control shampoo is too high suggesting that the tickling does not provide enough stress on the fiber that actual combing does to reopen the split end.

U.S. Pat. No. 6,258,348 described a hair conditioning composition specifically for mending split ends. The composition consists of a ternary mixture of guar (cationic or amphoteric), a betaine based polyurethane surfactant, and a silicone polyurethane. This ternary blend can be incorporated into a cream rinse or a 2-in-1 shampoo to effectively mend split ends. The test method used to support mending for the example formulations in the patent consists of selecting ten split end fibers from a tress and then attaching them to a single tab tress. The single tab tress with the split end fibers are then subjected to the treatment such as shampooing and left to air dry. Split end repair is then evaluated under a magnifying glass. Percent mending is then reported. Their findings indicate that a high percentage of mending occurs with 2-in-1 shampoos containing a ternary blend of ingredients compared to the same composition with only two of the three components. One drawback with this method is that the permanence of the mend was not studied, only the initial mending. Also, combing ten fibers is not a realistic amount of hair that would impart enough stress during the combing process.

U.S. Pat. No. 4,900,545 described that a composition of panthenol, glucose, PVP and phytantriol could regenerate hairs that have been split. This result was tested on 100 hairs all of which had been split by mechanical or electrostatic pretreatment. The hairs were treated 10 minutes with the undiluted preparations of examples 1 through 7 therein. The hairs were then rinsed with tap water, dried and combed. The visually discernable split ends remaining were then determined by counting. The percentage of split ends remaining for the 7 formulas ranged from 10 to 50%. This method suffers because 100 fibers is not a sufficient mass of fibers when passed through the comb to subject the hair to sufficient bending to cause the hairs to split.

U.S. Pat. No. 6,251,379 disclosed that hair compositions containing a combination of quaternized keratose and a defined silicone derivative can mend split ends. The method to substantiate this effect consisted of using bundles of Asian type hair, treating them with the composition, and drying with combing and blow drying. The hair is then brushed another ten times. Split end mending is assessed both before and after treatment. Although there is a standard for judging the degree of the prevention of re-splitting, it appears that the assessment is qualitative in nature. One positive with this method, however, is the fact that it assesses split end repair after the hair is brushed.

U.S. Pat. No. 6,139,851 described that a hair cream based on a lower alcohol in oil type emulsion containing silicone derivatives to mend split ends. The method is the same as is described in U.S. Pat. No. 6,251,379. No quantitative assessment of split end repair was described suggesting to a greater extent than the previous patent that a qualitative assessment of split end repair was used.

Ramachandran in WO 96/32920 described an improved hair rinse composition. They claim that their hair rinse composition not only conditions hair to provide such properties as wet detangling, but also lends fixative properties and repairs split ends. The three main ingredients that comprise the rinse are quaternary ammonium salts, water insoluble acrylic or acrylate polymers and a solvent that comprises a long chain alcohol and/or alcohol ethoxylate. The solvent was used to compatibilize the quat and polymer. It is theorized, but no proof is shown, that the quaternary surfactant and polymer form a complex with each other in the solvent. It was also theorized that this complex is deposited during the rinse cycle of this hair conditioning composition which provides the function of both conditioning and styling that normally are contradictory to one another when formulated in the same product. Proof of this is supplied by running panel tests on hair swatches for ease of combing and stiffness in hair characteristic panel studies using tresses. It was found in all cases that high scores are obtained for these two hair characteristics when hair was treated with rinses containing the quat-polymer-solvent complex.

Split end mending also was measured therein using a Salon panel study. The procedure consisted in essence of a cycle of washing, drying, counting, treating, combing and counting. Counting split ends consisted of bundling the hair on the head in discrete sections. Using magnifying binoculars, 100 hairs were counted in each section and the number of split ends calculated for the whole head. Experimental results proved that the rinse containing the complex mended split ends. It was also determined that the degree of split end mending was dose related and increased with the number of treatments. They theorized that split end mending is achieved by the adhesiveness of the polymer. The thin layer of polymer that remains on the inner surfaces of the split ends after drying holds the splits together. The method relies heavily on counting split end fibers and statistical analysis of the data.

SUMMARY OF THE INVENTION

Split ends are one manifestation of hair damage, which are caused by physical, mechanical and chemical means.

Accordingly, it is an object of this invention to provide a composition to repair split ends.

Another objective is to provide an improved methodology for the assessment of repair of split ends.

Still another object herein is to provide a new methodology using stereomicroscopy, to observe mending and subassembly of the hair fiber, as well as the permanence of the mend.

In this invention, the inventors surprisingly discovered that compositions of a polyelectrolyte complex (PEC) having a microgel structure formed between a cationic polyquaternium polymer and an anionic polymer at a defined charge or mole ratios provides a high percentage of mending split ends after low stress combing in a leave-on treatment.

What is disclosed herein is a hair care composition for mending split ends comprising a polyelectrolyte complex between (a) a cationic polyquaternium polymer, and (b) an anionic copolymer containing mono-, di- or tri-acid groups, or salts thereof, in a charge ratio of (a):(b) of 0.82 to 1.80, preferably 0.90 to 1.50.

Examples of such cationic polyquaternium polymers are polyquaternium compounds including, but not limited to, Polyquaternium 6, 10, 11, 7, and 28 which have trade names as Merquat®, Polyquta®, Gafquat®, Conditioneze® 7 and Conditioneze® 28 respectively. Quaternized polysaccharides are other examples of suitable cationic polymers, e.g. Guar Hydroxypropyltrimonium chloride having the trade name Jaquar® (Rhodia).

Examples of anionic polymers are those polyacids containing mono-, di- or tri-acids monomer or their neutralized salt. The polyacids containing di-acids units include, but are not limited to, polyvinylmethyl/maleic acid (PVM/MA) copolymer which has a trade name Gantrez® S-97 (ISP). Example of polyacid or salt with a mono-acid unit include, but not limited to, the acrylic acid copolymers, or their salts, such as vinylpyrrolidone/acrylates/lauryl methacrylate copolymer which has a trade name of Styleze® 2000 (ISP).

Additional examples of cationic and anionic polymers of synthetic or natural origin can be found in the following treatises which disclose ingredients used in the personal care industry, and are included herein for reference: *Encyclopedia of Polymers and Thickeners, Cosmetic and Toiletries*, Vol. 117, No. 12. Dec. 2002; *Cosmetic Raw Material Analysis and Quality*, Chapter 3, IFSCC, Monograph, 2004; *Principles of Polymer Science and Technology in Cosmetics and Personal Care*, 1999, Appendix.

A typical cationic polymer for forming the PEC has the chemical structure set forth below.

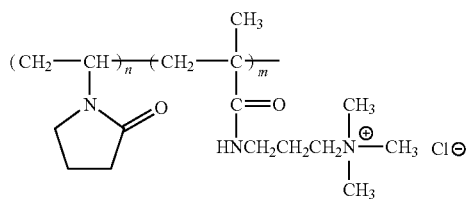

Conditioneze® NT-20 (Polyquaternium-28) (wt. Molecular wt. of ~1 Million, and a Weight Ratio of n and m of 85:15)

The chemical structure of a typical anionic polymer which form the polyelectrolyte complex in this invention is:

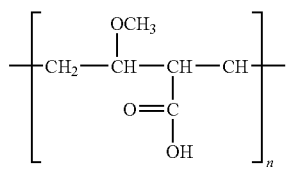

Gantrez® S-97 (PVM/MA Copolymer) (Specific Viscosity of Gantrez AN 169 is 2.5 to 3.5) (1% in MEK 25° C.)

By controlling the charge ratios of the two oppositely charged polymers, the complexation of the polymers can lead to the formation of a microgel structure.

The PEC microgels have a particle size ranging from 0.5 μm to 31 μm, preferably from 3 to 15 microns.

The charge ratio of the cationic to anionic polymers range from 0.82-1.80, preferably 0.90 to 1.5.

The mole ratio of the quaternium unit of the cationic polymer to the anionic polymer is the charge ratio times $n_a/n_c$, where $n_a$ is the total number of anionic groups in one monomer unit of the anionic polymer and $n_c$ is the total number of quaternary groups in one monomer unit of the cationic polymer.

For example, the $n_a$ of the anionic polymer polyvinylmethyl/maleic acid (PVM/MA), is 1.7 at pH 7, considering that one acid group having a low pKa is fully ionized and the other acid group having a higher pKa is 70% ionized, giving the total anionic number of 1.7 in its one monomer unit. Therefore, the mole ratio of the quaternium unit of the mono cationic polymer polyquaternium-28 to the anionic polymer containing a di-acid unit such as polyvinylmethyl/maleic acid (PVM/MA) is 1.39 to 3.06, preferably is 1.50 to 2.55.

Accordingly, the mole ratio of the quaternium unit of the cationic polymer to anionic polymer wherein the anionic polymer contains a mono-acid unit such as vinylpyrrolidone/acrylates/lauryl methacrylate is 0.82 to 1.80, preferably is 0.90 to 1.50.

The weight ratio of the cationic polymer to the anionic polymer is the mole ratio times MWc times the wt. % of quaternary unit in the cationic polymer divided by MWa times the wt. % of the acid unit in the anionic polymer. MWc is the molecular weight of the monomer unit in the cationic polymer and MWa is the molecular weight of the monomer unit in the anionic polymer. For example, the weight ratio of a mono cationic polymer, e.g. polyquaternium-28, to the anionic polymer containing a di-acid unit such as polyvinylmethyl/maleic acid (PVM/MA) is 6.5 to 14.30, preferably from 7.0 to 11.91.

Accordingly, the weight ratio of the cationic polymer e.g. polyquaternium-28, to the anionic polymer wherein the cationic polymer contains a mono-acid group, e.g. vinylpyrrolidone/acrylates/lauryl methacrylate, is 2.44 to 5.37, preferably from 2.68 to 4.47.

The polyelectrolyte complex microgels formed within the defined ratio range of the cationic and anionic polymers provide at least 30% mending before combing and at least about 15% durability after combing.

Accordingly, what is described herein is a hair care composition for mending damaged hair fibers comprising polyelectrolyte complex microgels between anionic and cationic polymers.

IN THE DRAWINGS

DETAILED DESCRIPTION OF THE INVENTION

This application deals with one form of hair repair, specifically split end mending. This invention provides a polyelectrolyte complex composition formed between cationic and anionic polymers for split ends repair.

A complex is formed herein between two polymers interacting through non-covalent bonding e.g. ionic, hydrogen, or an associative mechanism of hydrophobic groups on the molecule. In the preferred example herein, two oppositely charged polymers interact through their cationic and anionic charges to form a polyelectrolyte complex in the form of a microgel.

In a hair care composition of this invention, the polyelectrolyte complex in the form of microgels having a particle size in the range of 0.5 µm to 31 microns are small enough to infiltrate the fissures of the split cortex and the lifted cuticle which is also present in the damaged hair. During this stage the residual cationic charges on the microgel bind to the anionic sites of the damaged cortex and form a cationic linkage. The adhesive crosslinking structure of the microgel then fuses the damaged parts of the fiber together. During the drying stage the microgel complex is able to form a dry film that coats and seals the lifted cuticles and the split end together. The unique features of the dried film of the microgels ensure a durable mending that will survive a post-combing process which is typical of normal styling behavior.

Figure 1:
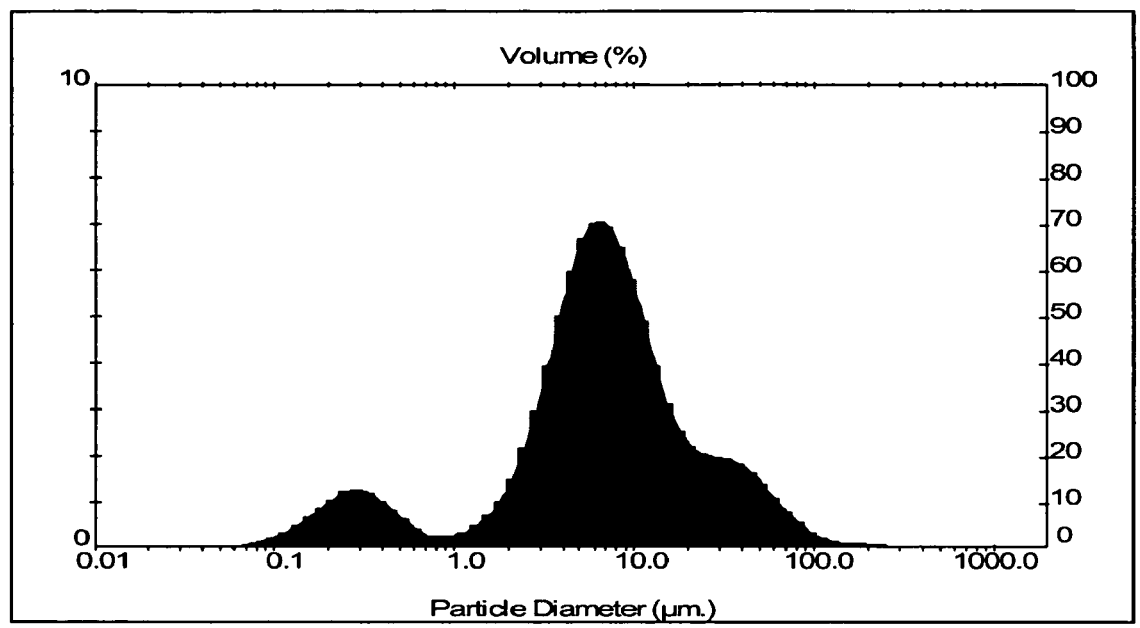
FIG. 1 is a graphical plot of particle size distribution of PEC microgels.

The particle size distribution of microgels of the complex of the invention in water was measured using a Malvern Mastersizer S. This instrument determines the particle size distribution of liquid dispersions using Mie laser light scattering theory. The particle size distribution curve of the complex is shown in FIG. 1. The particle size distribution data indicates that the microgel particles have a mean diameter of 6.70 µm and the size ranges from 0.53 µm at 10% distribution to 31.68 µm at 90% distribution.

One preferred example of a cationic/anionic polymer polyelectrolyte complex in this invention is a complex of Gantrez® S-97 and Conditioneze® NT-20 used in a leave-in treatment. At a defined preferred cationic/anionic ratio the polyelectrolyte complex is present as microgels as illustrated in the example below. In this system, the cationic nature of Conditioneze® NT-20 contributes to the residual cationic charges on the microgels forming cationic linkages to the anionic sites on the hair surface. Then the PEC microgels' adhesive crosslinking structure can glue the two split fibers and seal them on drying through the dry film formed. The example below shows that maximum split end mending efficacy is achieved at a 1:1 charge ratio of the two polymer units.

This invention also provides an improved method for assessing split end repair to substantiate the ability of a polyelectrolyte complex formed between anionic and cationic polymers to repair this type of hair damage. The major feature of the improved test method used for the assessment of split end repair consists of tagging particular split ends fibers in a hair tress. The tagging allows the study of the fate of that particular split end, and importantly subjecting it to normal combing stresses in order to determine the permanence of the mend.

Test Methods for Assessing Split End Repair Performance

Materials:
  Hair tresses are from International Hair Importers. Hair type is virgin brown that has been sewn to 1¾" across with 3.5 grams of loose hair, 6.5" in length from bottom of binding to tip.
  Plastic comb from Sally's Beauty Supply, having a fine comb density of 8 prongs per centimeter.
  Tweezers.
  Hand held magnifying glass (1.2×).
  Tags made from thin strips of Scotch tape.
  Permanent Marker.

Equipment

Thermal/Mechanical Styling Apparatus with two brushes

Nikon SMZ 1500 Stereomicroscope

Linksys 2.2 program for digital imagery from microscope
  Linksys for Windows
  Linkam Scientific Instruments Inc.
  8 Epsom Downs Metro Center, Waterfield
  Waterfield, Tadsworth, Surrey
  KT205HT England Procedure 1) Producing Split Ends Virgin brown hair tresses were supplied from International Hair Importers. Hair has been sewn to 1¾" across with 3.5 grams of loose hair. Hair tress is 6.5" in length from bottom binding to tip end.

To produce split ends thermal mechanically, hair tresses were first rinsed for 10 seconds and soaked in 2% sodium hydroxide solution for five minutes. Hair tresses were then rinsed and combed through with a plastic comb from Sally's Beauty Supply to remove the initial snags. Hair tress was then put on a thermal/mechanical styling apparatus for 1.5 hours at 75 rpm at low speed (two brushes per revolution). A hair blow dryer was set at warm and low speed pointing at the middle of the tress. Brush was set to a position to hit at least ¾ of tress length. At the end of the process, the hair tress was examined under light to confirm that it is easy to find 20 split ends across the hair tress. If not more time of brushing is needed until satisfactory number of split ends are produced.

2) Pretreatment of Hair Tress

1. Isolate a split end and carefully draw a dot with a red permanent marker slightly before the beginning of the split to later determine if the split broke off after combing. Label the split fiber at root end. Repeat the procedure for 20 split ends for each tress. Choose splits uniformly distributed through tress.

2. Take pictures under stereomicroscope (20×) and save the pictures defined as pretreatment.

3. Record split end data as 1=end split, 0=no split, 0.5=partial split for each primary, secondary and tertiary split.

3) Post Treatment and without Combing the Hair Tress

1. Wash the tress with 3% ALS and rinse well.

2. Apply 0.50 g of formula to damp hair tress and work it through so that it is totally distributed through the hair. Dry it in the hood.

3. Gently stroke tress with fingers to break crust.

4. Take pictures as in step 2 for tagged fibers defined as post treatment before combing.

5. Record split end as in step 3.

4) Post Treatment with Combing the Hair Tress (Durability)

1. Comb the hair tresses twenty times with fine tooth comb.

2. Take pictures of tagged fibers for split end repair.

3. Inspect tress to see permanent mark against false positives.

4. Record split end as in step 3.

5) Calculations from Data $$\text{Total Mending}\% = \frac{(\text{split number before treat} - \text{after treatment})}{\text{Split number before treatment}}$$

Scoring 1 = split end, 0 = mended split, 0.5 = partially mended split $$\text{Durability Index } D = \frac{\text{Total mending}\% \text{ after combing}}{\text{Total mending}\% \text{ before combing}}$$

Therefore, the maximum $D = 1.0$ and minimum $D$ is 0.

Procedure to Prepare PEC Complex

PEC complex was prepared in the following procedures as exampled with Polyquaternium 28 (Conditioneze NT-20) and Polymethylvinyl ether/maleic acid (Gantrez S-97).

1) Preparation of Stock Solutions of the Polymers

| Batch A: 4% active Gantrez S-97 Solution | % W/W | SUPPLIER |
|---|---|---|
| Water | 84.73 | |
| Sodium Hydroxide (10.00% active) | 11.27 | |
| PVM/MA Copolymer (Gantrez ® S-97) (100% active) | 4.0 | ISP |
| | 100.00% | |

Note:
In order to neutralize the Gantrez S-97, a 1:2.7 ratio of polymer to 10% NaOH solution was used to produce a pH of 7.

Procedure:

1. Add water to main tank. Mix with propeller blade.
2. Sprinkle Gantrez S-97 into vortex.
3. Add Sodium Hydroxide and mix until uniform.

| Batch B: 4% active Conditioneze NT-20 Solution | % W/W | SUPPLIER |
|---|---|---|
| Water | 80.49 | |
| Polyquaternium-28 (Conditioneze ® NT-20) (20.5% active) | 19.51 (4% active) | ISP |
| | 100.00% | |

Batch C: 4% Complex Solution, Concentrate

Procedure:

Add 45 parts of Batch B, 4.00% active aqueous solution of Conditioneze® NT-20, to main container and mix with moderate to fast (1000-1200 rpm) propeller agitation. Add 5 parts of Batch A, 4.00% active Gantrez® BF Polymer S-97 solution, to Conditioneze® NT-20 solution over the course of about 20-30 seconds. Mix for ten minutes.

| Appearance of PEC complex: | thin, milky-white liquid |
|---|---|
| pH: | 7.13 |

The 4% complex concentrate is diluted to 2% active either with water or formulated into a leave in treatment product. This is then applied to hair.

Directions of use: Massage lotion into damp hair concentrating especially at the ends. Comb product through hair and style.

Figure 2:
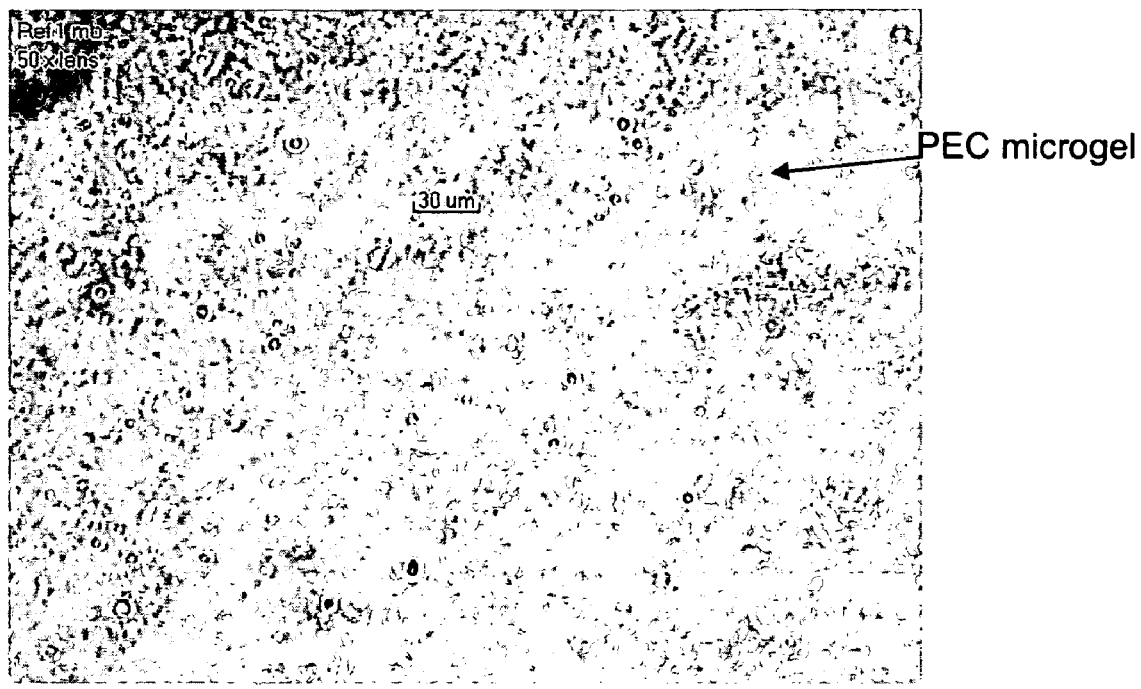
FIGS. 2, 2a, 2b and 2c are optical microscope images of polyelectrolyte complex microgels of the invention.

Table 1 shows some examples of the polyelectrolyte compositions within the scope of this invention. FIG. 2 shows a typical microscope image of the PEC microgels of Example 1 composition.

TABLE 1

| Ingredients INCI name | Trade name | EXP. 1 WT. % | EXP. 2 WT. % | EXP. 3 WT. % | EXP. 4 WT. % | EXP. 5 WT. % |
|---|---|---|---|---|---|---|
| Polymethylvinyl ether/maleic acid | Gantrez ® S-97 | 0.20 | 0.10 | 0.30 | 0.40 | 0.15 |
| NaOH, 10% Neutralizing agent | | 0.56 | 0.27 | 0.38 | 1.12 | 0.19 |
| Polyquaternium-28 | Conditioneze ® NT-20 | 1.80 | 1.0 | 2.8 | 4.0 | 1.5 |
| Water | | BAL | BAL | BAL | BAL | BAL |

Examples 6-9

Figure 2A:
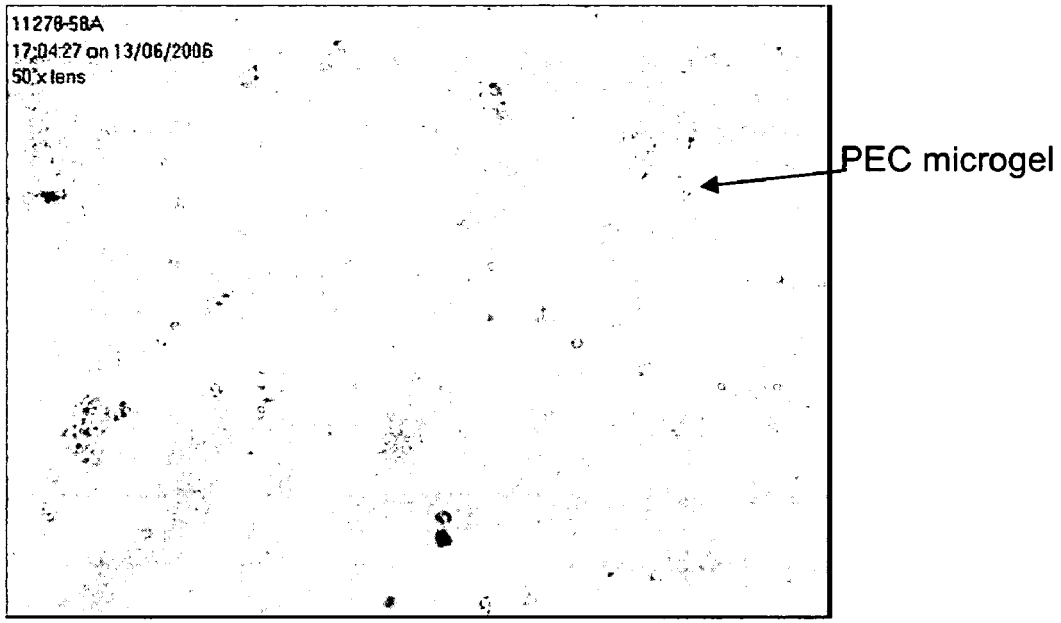
Figure 2B:
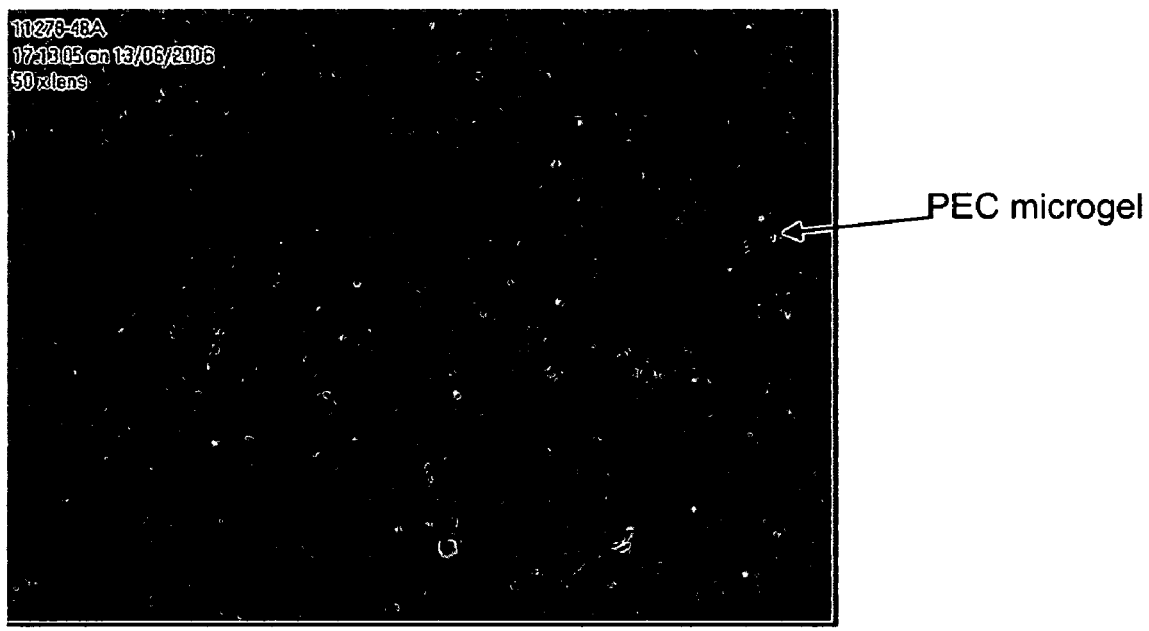
Figure 2C:
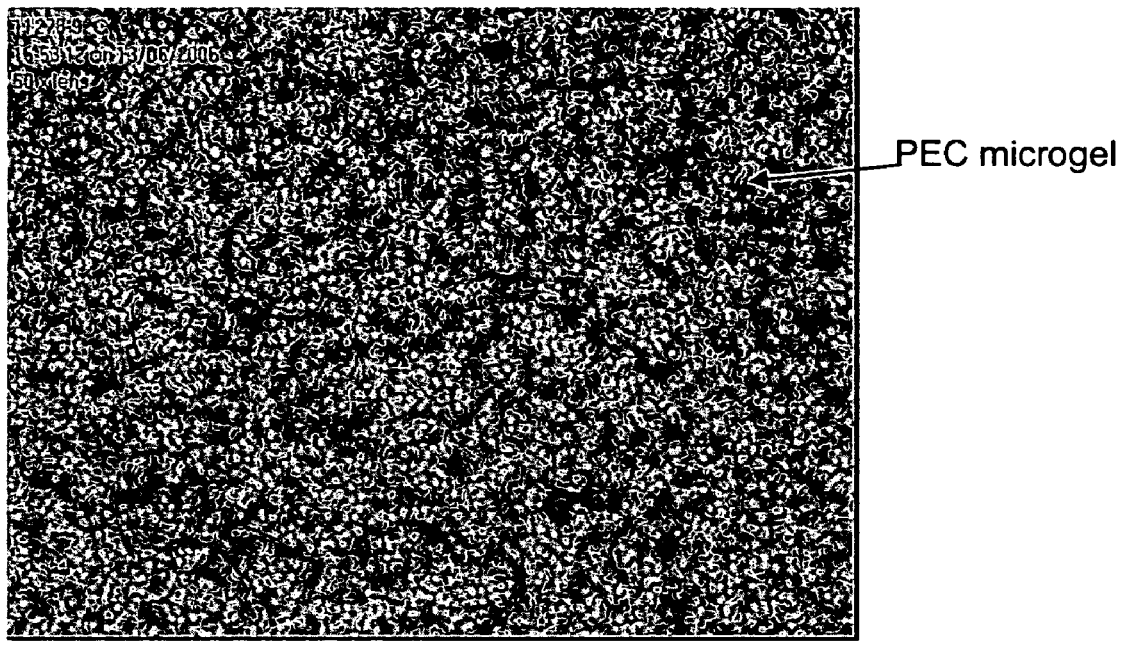
Figure 2D:
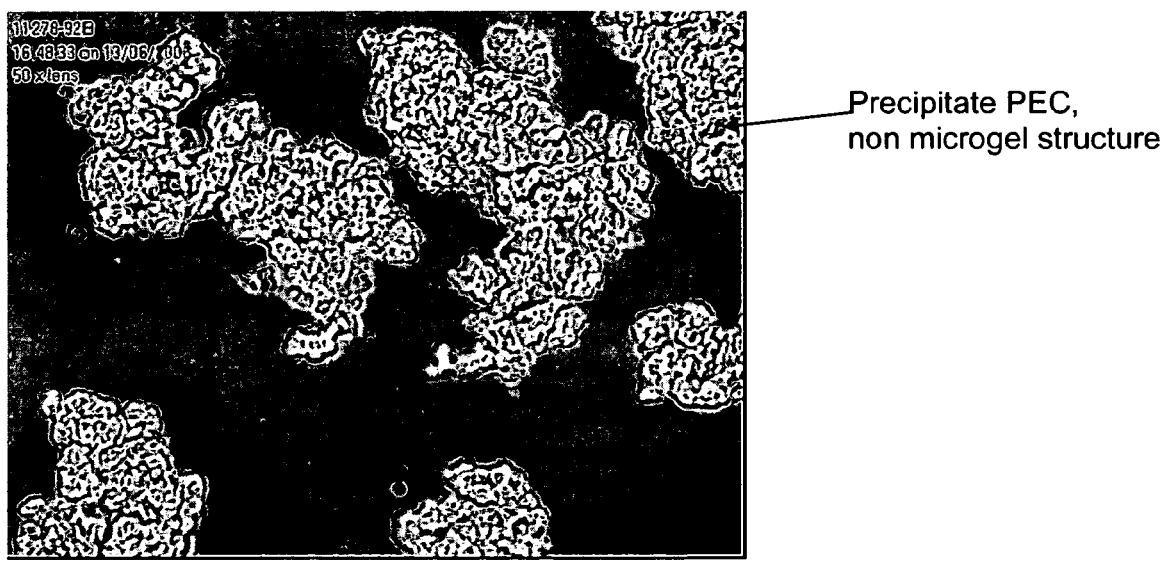
FIG. 2d is an optical microscope image of polyelectrolyte complex precipitate not typical of the microgel structures of the invention.

Table 2 below shows other examples of polyelectrolyte compositions within the scope of this invention. FIGS. 2a, 2b and 2c show the microscopic images of polyelectrolyte microgel particles of Examples 7, 8 and 9a. As a comparison, Example 9b, a composition of the two oppositely charged polymers of Example 9a but having a charge ratio outside the range defined in this invention is also listed in Table 2, its microscopic images in FIG. 2d show a large aggregate of precipitate rather than a desired, uniformly dispersed microgel structure.

TABLE 4-continued

| INGREDIENTS | Example 10 % W/W | Example 11 Comparative % W/W | SUPPLIER |
|---|---|---|---|
| Propylene glycol (and) Diazolidinyl Urea and Iodopropynyl Butylcarbamate (liquid Germall Plus) | 0.50 | 0.5 | ISP |

TABLE 2

| Polymer type | Ingredients INCI name | Trade name | EXP 6 WT. % | EXP 7 WT. % | EXP 8 WT. % | EXP 9a WT. % | EXP 9b WT. % |
|---|---|---|---|---|---|---|---|
| Anionic, mono-acid unit | Vinylpyrrolidone/ acrylates/lauryl methacrylate copolymer | Styleze 2000 | | 0.51 | | | |
| Cationic, monoquat unit | Polyquternium 28 | Conditioneze NT-20 | | 1.49 | | | |
| Anionic, di-acid units | Polymethylvinyl ether/maleic acid | Gantrez S-97 | 0.25 | | 0.25 | 0.25 | 0.25 |
| Cationic, monoquat unit | Polyquaternium 7 | Conditioneze 7 | | | | 1.75 | 1.25 |
| Cationic, monoquat unit | Polyquaternium 10 | Polyquta 400 KC | | | 1.75 | | |
| Cationic, monoquat unit | Polyquaternium 11 | Gafquat 755 | 1.62 | | | | |
| | NaOH, 10% Neutralizing agent | | 0.67 | 0.56 | 0.67 | 0.67 | 0.67 |
| | water | BAL | BAL | NAL | BAL | BAL | BAL |
| | Charge ratio | | 1.0 | 0.98 | 0.93 | 1.13 | 0.81 |
| | Mole ratio | | 1.7 | 0.98 | 1.58 | 1.93 | 1.38 |
| | Weight ratio | | 6.50 | 2.92 | 7.0 | 7.0 | 5.0 |
| | Forming microgel | | yes | yes | yes | yes | No |

Examples 10-11

These examples demonstrate the effectiveness of PEC formulated into a cosmetic composition in mending hair split end. The composition of Example 10 is shown in Table 4, it contains the PEC microgel. As a comparison, the same composition but without the complex (Example 11) was also tested. Table 5 lists the mending test results for the two compositions. The results show that the composition containing the PEC complex achieves 93% mending before combing, and 67% mending after combing, while the control formulation (without the complex) achieved only 50% and 12.9% mending, respectively, demonstrating the effectiveness of the PEC complex in mending split ends.

TABLE 4

| INGREDIENTS | Example 10 % W/W | Example 11 Comparative % W/W | SUPPLIER |
|---|---|---|---|
| Water | 49.0 | 99 | |
| Xanthan Gum (Rhodicare T) | 0.50 | 0.5 | Rhodia |
| PEC Complex, 4% active (Batch C) | 50 | 0 | ISP |

TABLE 5

Mending test results for Examples 10 and 11

| | Example 10 With complex | | Example 11 No complex | |
|---|---|---|---|---|
| Mending % | Before comb | After comb | Before comb | After comb |
| Tress 1* | 95 | 57.5 | 65.8 | 15.8 |
| Tress 2* | 92.5 | 82.5 | 50.4 | 12.9 |
| Tress 3* | 89.5 | 76.3 | 50 | 13 |
| Tress 4* | 95 | 52.5 | 63 | 11 |
| Tress 5* | 94.4 | 69.4 | 50 | 12 |
| Average | 93.2 | 67.6 | 50.4 | 12.9 |
| Standard deviation | 2.3 | 12.6 | 9.2 | 1.6 |

*Each tress has 20 tagged split end fibers

Example 12

Figure 3:
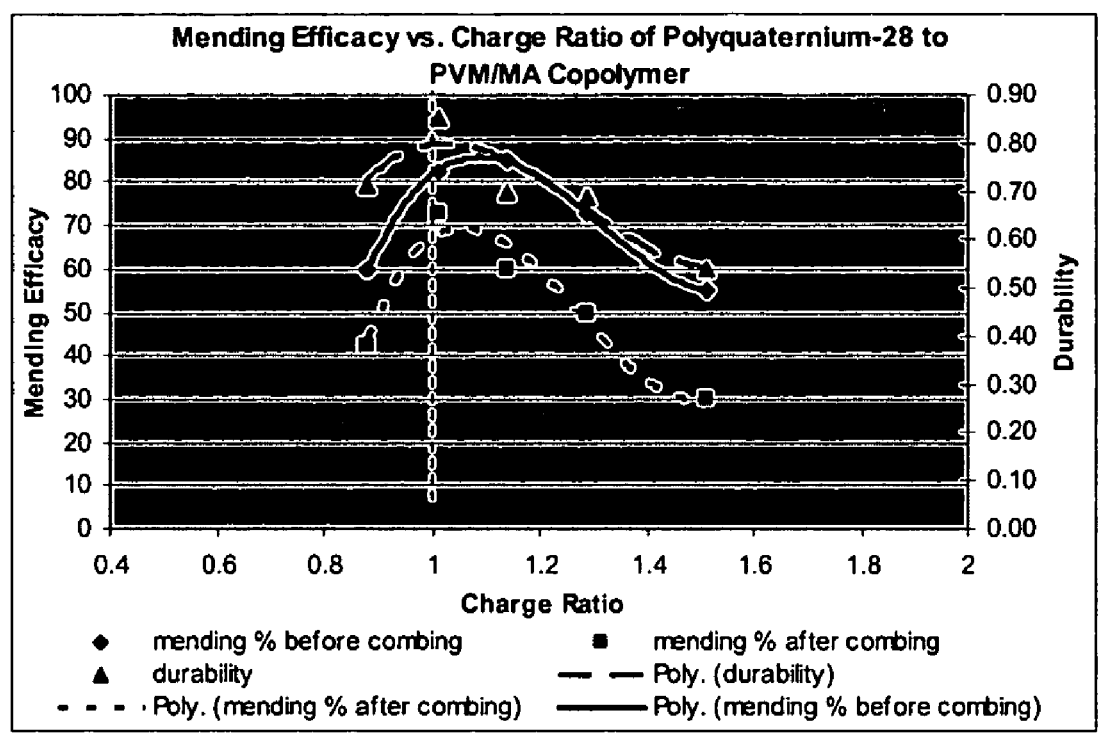
FIG. 3 is a graphical representation of mending efficacy of PEC hair care compositions vs charge ratios of cationic to anionic polymers therein.

This example further demonstrates the effectiveness of the polyelectrolyte compositions within the scope of this invention to repair hair split ends mending efficacy. Polyelectrolyte compositions with varying charge ratios listed in Table 6 were assessed for mending efficacy. Table 7 and FIG. 3 show the mending test results. The results demonstrate that the polyelectrolyte compositions with charge ratios within our defined ranges achieve maximum efficacy of hair split end repair.

TABLE 6

PEC Compositions with Varying Charge Ratios

| Ingredients INCI name | Trade name | 12a Wt % | 12b Wt % | 12c Wt % | 12d Wt % | 12e Wt % |
|---|---|---|---|---|---|---|
| Polymethylvinyl ether/maleic acid | Gantrez S-97 | 0.20 | 0.20 | 0.20 | 0.20 | 0.20 |
| NaOH, 10%, neutralizer | | | 0.54 | 0.54 | 0.54 | 0.54 |
| Polyquaternium 28 | Conditioneze NT-20 | 1.4 | 1.8 | 2.0 | 2.6 | 1.6 |
| water | | to 100 | to 100 | to 100 | to 100 | to 100 |

TABLE 7

Mending Test Results of Compositions of Table 6

| | 12a Wt % | 12b Wt % | 12b Wt % | 12d Wt % | 12e Wt % |
|---|---|---|---|---|---|
| Charge ratio | 0.88 | 1.29 | 1.14 | 1.51 | 1.01 |
| Mending efficacy, % Before combing | 60.0 | 72.5 | 85.0 | 55 | 82.5 |
| Mending efficacy, % After combing | 42.5 | 50 | 60.0 | 30.0 | 72.5 |
| Durability after Combing | 0.71 | 0.69 | 0.70 | 0.54 | 0.85 |

Example 13

This example shows the mending efficacy of a PEC composition of 1.75% Polyquaternium 7 (Conditioneze NT-7) and 0.25% Gantrez S-97.

TABLE 8

Composition of Example 13

| Ingredient | INCI name | Wt % |
|---|---|---|
| Gantrez S-97, 4% active | Polymethylvinyl ether/maleic acid | 6.25 |
| NaOH, 10%, Neutralizer | | 0.675 |
| Conditioneze-7, 4% active | Polyquaternium 7 | 43.75 |
| Germall plus (preservative) | | 0.20 |
| Water | Water | To 100 |

TABLE 9

Mending Test Results of Example 13

| | Before treatment | | | After leave-in treatment | | | After treatment and after combing | | |
|---|---|---|---|---|---|---|---|---|---|
| Fiber # | P* | S* | T* | P* | S* | T* | P* | S* | T* |
| 1 | 1 | | | 0 | | | 0 | | |
| 2 | 1 | | | 1 | | | 1 | | |
| 3 | 1 | | | 0 | | | 0 | | |
| 4 | 1 | 1 | | 1 | 0 | | 1 | 1 | |
| 5 | 1 | | | 0 | | | 0 | | |
| 6 | 1 | | | 1 | | | 1 | | |
| 7 | 1 | | | 1 | | | 1 | | |
| 8 | 1 | | | 1 | | | 1 | | |
| 9 | 1 | | | 1 | | | 1 | | |
| 10 | 1 | | | 0 | | | 0 | | |
| 11 | 1 | 1 | | 0 | | | 0 | | |

TABLE 9-continued

Mending Test Results of Example 13

| | Before treatment | | | After leave-in treatment | | | After treatment and after combing | | |
|---|---|---|---|---|---|---|---|---|---|
| Fiber # | P* | S* | T* | P* | S* | T* | P* | S* | T* |
| 12 | 1 | | | 1 | | | 1 | | |
| 13 | 1 | | | 0 | | | 0 | | |
| 14 | 1 | | | 1 | | | 1 | | |
| 15 | 1 | | | 0 | | | 0 | | |
| 16 | 1 | | | 0 | | | 1 | | |
| 17 | 1 | | | 1 | | | 1 | | |
| 18 | 1 | | | 0 | | | 0 | | |
| 19 | 1 | | | 1 | | | 1 | | |
| 20 | 1 | | | 1 | | | 1 | | |
| # of split end | 20 | | | | | | | | |
| # of mended fibers | | | | 8 | | | 7 | 1 | |
| Mending % | | | | 42 | 100 | | 37 | 50 | |
| Durability** | | | | | | | 0.89 | 0.5 | |

*P = primary split end, S = secondary split end, T = tertiary split end Scoring 1 = split end, 0 = mended split, 0.5 = partially mended split
**Durability = 0 (minimum) to 1.0 (maximum)

Example 14

Mousse Composition of PEC Microgels

TABLE 10

| Ingredients | Trade Name | W/W % |
|---|---|---|
| PEC, Batch C*, 4% active | Gantrez S-97, Conditioneze NT-20 | 50.1 |
| Cap 40, Propellant | | 6.0 |
| Water | | 43.9 |

*Batch C: 4% complex solution, concentrate

Procedure:

To prepare batch C, add 45 parts of Batch B, 4.00% active aqueous solution of Conditioneze® NT-20, to main container and mix with moderate to fast (1000-1200 rpm) propeller agitation. Add 5 parts of Batch A, 4.00% active Gantrez® BF Polymer S-97 solution (neutralized), to Conditioneze® NT-20 solution over the course of about 20-30 seconds. Mix for ten minutes.

Fill PAM lined AL cans at 100 g fill and Wheaton bottles at 50 g fill at 94/6 PEC Concentrate/Propellant ratio. Shake well.

Wait 30 minutes, shake well and test for foam quality. The quality of the foam of this mousse tends to crackle when dispensed which is advantageous in use.

Example 15

Treatment Cream Containing PEC Microgels

TABLE 11

| Ingredients | Trade name | W/W % | Phase |
|---|---|---|---|
| Water | | 44.08 | A |
| Xanthan Gum | | 0.50 | A |
| Isocetyl stearate | Ceraphyl 494 | 4.00 | B |
| Polyglyceryl-4 and PEG-8 Propylene Glycol Cocoate | Emulsgnt 1055 | 0.70 | B |
| PEG-20 Stearate | Cerasynt 840 | 0.30 | B |
| PEC, Batch C*, 4% active | Gantrez S-97 ®, Conditioneze NT-20 ® | 50.1 | C |
| Germall plus (preservative) | | 0.50 | D |

*See Example 14.

Procedure to Prepare Example 15:

Add xanthan gum to water and heat to 75° C. with mixing until uniform. In a separate container, add ingredients of phase B, heat with mixing to 75° C. When uniform, add phase B to Phase A and mix until uniform, cool to 30° C. and add Phase C (refer to Example 10). Mix until uniform, add Phase D and mix until uniform.

While the invention has been described with particular reference to certain embodiments thereof, it will be understood that changes and modifications may be made which are within the skill of the art. Accordingly, it is intended to be bound only by the following claims, in which:

What is claimed is:

1. A hair care composition for mending split ends comprising a polyelectrolyte complex between
   (a) a cationic polyquaternium polymer and
   (b) an anionic copolymer containing mono-, di- or tri-acid groups, or salts thereof, in a charge ratio of (a):(b) of 0.82 to 1.80;
   wherein said polyelectrolyte complex has a microgel structure.

2. A hair care composition according to claim 1 wherein said charge ratio is 0.90 to 1.50.

3. A hair care composition according to claim 1 wherein said charge ratio is 1.

4. A hair care composition according to claim 1 wherein the particle size is 0.5 μm to 31 μm.

5. A hair care composition according to claim 4 wherein said particle size is 3 to 15 microns.

6. A hair care composition according to claim 1 which is a thin milky-white liquid.

7. A hair care composition according to claim 1 wherein the mole ratio of the quaternium unit of said cationic polyquaternium polymer to said anionic copolymer provides a charge ratio times $n_a/n_c$ where $n_a$ is the total number of anionic groups in one monomer unit of the anionic copolymer and $n_c$ is the total number of quaternary groups in one monomer unit of the cationic polymer.

8. A hair care composition according to claim 1 wherein the weight ratio of said cationic quaternium polymer to said anionic copolymer is provided by a mole ratio times MWc times wt % of quaternary unit in cationic polymer divided by MWa times wt % of the acid unit in anionic polymer where MWc is the monomer molecular weight of the cationic polymer and MWa is the monomer molecular weight of the anionic polymer.

9. A hair care composition according to claim 1 wherein (a) is polyquaternium-6, 7, 10, 11, 22 or 28.

10. A hair care composition according to claim 1 wherein (a) is quaternized polysaccharide.

11. A hair care composition according to claim 9 wherein (a) is polyquaternium-28.

12. A hair care composition according to claim 9 wherein (b) is polyvinylmethyl/maleic acid (PVM/MA) copolymer.

13. A hair care composition according to claim 9 wherein (b) is a copolymer of vinylpyrrolidone/acrylates/lauryl methacrylate.

14. A hair care composition according to claim 12 wherein the mole ratio of the quaternium unit of (a):(b) is 1.39 to 3.06.

15. A hair care composition according to claim 13 wherein the mole ratio of said quaternium unit of (a):(b) is 0.82 to 1.80.

16. A hair care composition according to claim 12 wherein the mole ratio of the quaternium unit of (a):(b) is 1.50 to 2.55.

17. A hair care composition according to claim 13 wherein the mole ratio of said quaternium unit of and (a):(b) is 0.90 to 1.50.

18. A hair care composition according to claim 14 wherein the mole ratio of said quaternium unit of (a):(b) is 1.7.

19. A hair care composition according to claim 15 wherein the mole ratio of said quaternium unit of (a):(b) is 1.0.

20. A hair care composition according to claim 14 wherein the weight ratio of (a):(b) is 6.5 to 14.30.

21. A hair care composition according to claim 15 wherein the weight ratio of (a):(b) is 2.44 to 5.37.

22. A hair care composition according to claim 20 wherein the weight ratio of (a):(b) is 7.0 to 11.91.

23. A hair care composition according to claim 21 wherein the weight ratio of (a):(b) is 2.68 to 4.47.

24. A hair care composition according to claim 20 wherein the weight ratio of (a):(b) is 9.0.

25. A hair care composition according to claim 21 wherein the weight ratio of (a):(b) is 3.0.

26. A hair care composition according to claim 1 which has a mending efficacy before combing of at least 30%.

27. A hair care composition according to claim 26 wherein said mending efficacy is at least 50%.

28. A hair care composition according to claim 26 wherein said mending efficacy is at least 90%.

29. A hair care composition according to claim 1 which has a durability of mending after combing of at least 15%.

30. A hair care composition according to claim 29 wherein said durability is at least 25%.

31. A hair care composition according to claim 29 wherein said durability is at least 45%.

32. A hair care composition according to claim 1 which is a leave-in composition.

33. A hair care composition according to claim 32 which is a lotion, spray, cream, emulsion, mousse, or gel.

34. A hair care formulation according to claim 1 which includes said polyelectrolyte complex in an amount of about 0.1 to 10 wt % of said formulation.

35. A hair care formulation according to claim 34 including 0.5 to 5 wt % of said polyelectrolyte complex.

36. A hair care formulation according to claim 34 including 1 to 3 wt % of said polyelectrolyte complex.

37. A hair care formulation according to claim 34 wherein said polyelectrolyte complex comprises cationic and anionic polymers in a charge ratio of 0.9 to 1.5.

38. A method of mending split end fibers in hair tresses which comprises applying thereto the hair care composition of claim 1.

* * * * *